United States Patent
Rucker

(10) Patent No.: US 7,524,329 B2
(45) Date of Patent: Apr. 28, 2009

(54) SELF CONTRACTING STENT

(75) Inventor: Brian K. Rucker, King, NC (US)

(73) Assignee: Wilson-Cook Medical Inc., Winston-Salem, NC (US)

( * ) Notice: Subject to any disclaimer, the term of this patent is extended or adjusted under 35 U.S.C. 154(b) by 181 days.

(21) Appl. No.: 11/348,278

(22) Filed: Feb. 6, 2006

(65) Prior Publication Data

US 2006/0184231 A1  Aug. 17, 2006

Related U.S. Application Data

(60) Provisional application No. 60/651,028, filed on Feb. 8, 2005.

(51) Int. Cl.
*A61F 2/06* (2006.01)
(52) U.S. Cl. ............... 623/1.12; 623/903; 623/1.11; 623/1.18; 623/1.19; 606/192
(58) Field of Classification Search ............... 623/1.11, 623/1.12, 1.18, 1.19, 1.2, 1.23, 1.3
See application file for complete search history.

(56) References Cited

U.S. PATENT DOCUMENTS

| 3,174,851 | A | 3/1965 | Buehler et al. |
| 3,652,969 | A | 3/1972 | Wilson et al. |
| 4,304,613 | A | 12/1981 | Wang et al. |
| 5,037,427 | A | 8/1991 | Harada et al. |
| 5,197,978 | A | 3/1993 | Hess |
| 5,562,641 | A | 10/1996 | Flomenblit et al. |
| 5,716,410 | A | 2/1998 | Wang et al. |
| 5,746,765 | A | * 5/1998 | Kleshinski et al. ......... 128/898 |
| 5,830,179 | A | 11/1998 | Mikus et al. |

(Continued)

FOREIGN PATENT DOCUMENTS

EP  0411118 A1  2/1991

(Continued)

OTHER PUBLICATIONS

The International Search Report and Written Opinion for PCT/US2006/004098 mailed Jun. 1, 2006.

(Continued)

*Primary Examiner*—Thomas J Sweet
*Assistant Examiner*—Jonathan R Stroud
(74) *Attorney, Agent, or Firm*—Brinks Hofer Gilson & Lione

(57) ABSTRACT

A self-contracting stent for use at a treatment site comprising shape memory material is provided. The stent may have an initial diameter for delivery to the treatment site and an expanded diameter when deployed at the treatment site. The stent further may have a contracted diameter when subjected to a temperature at or above a transition temperature. The contracted diameter is less than the expanded diameter and permits repositioning or removal of the stent from the treatment site. Additionally, a method for delivering and recovering the stent from a treatment site is provided. The method includes delivering a stent to a treatment site and expanding the stent at the treatment site so that the stent is deployed at the treatment site. The method further includes changing the temperature of the stent at the treatment site to at least a transition temperature to cause the stent to contract.

11 Claims, 4 Drawing Sheets

U.S. PATENT DOCUMENTS

| | | | |
|---|---|---|---|
| 5,833,707 A * | 11/1998 | McIntyre et al. | 606/198 |
| 6,077,298 A | 6/2000 | Tu et al. | |
| 6,258,118 B1 | 7/2001 | Baum et al. | |
| 6,348,067 B1 | 2/2002 | Baum et al. | |
| 2002/0142119 A1 | 10/2002 | Seward et al. | |
| 2002/0161427 A1* | 10/2002 | Rabkin et al. | 623/1.11 |
| 2002/0177899 A1 | 11/2002 | Eum et al. | |
| 2004/0034405 A1 | 2/2004 | Dickson | |
| 2005/0187612 A1 | 8/2005 | Edwin | |
| 2007/0129784 A1* | 6/2007 | Lendlein et al. | 623/1.11 |

FOREIGN PATENT DOCUMENTS

| | | | |
|---|---|---|---|
| WO | WO 99/42147 | | 8/1999 |
| WO | PCT/EP2004/006262 | * | 12/2004 |
| WO | WO 2004/110313 A1 | | 12/2004 |
| WO | WO 2004/110515 A1 | | 12/2004 |

OTHER PUBLICATIONS

International Preliminary Report on Patentability, dated Mar. 6, 2007, for International Patent Application No. PCT/US2006/004098.

* cited by examiner

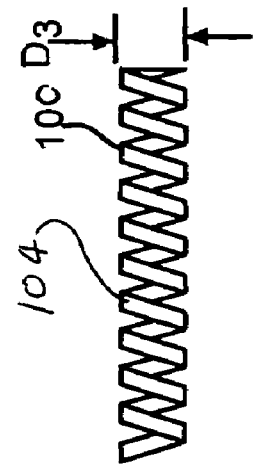 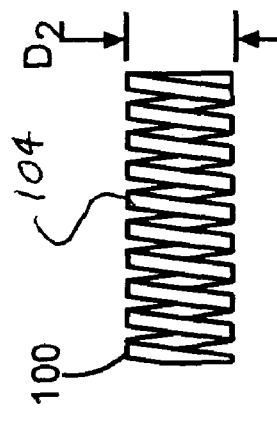 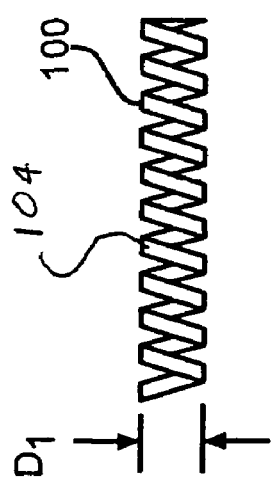
FIG. 1A   FIG. 1B   FIG. 1C
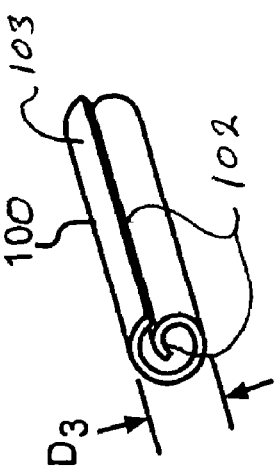 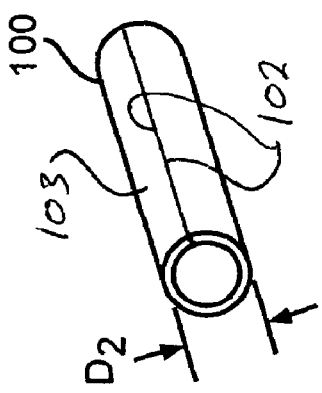 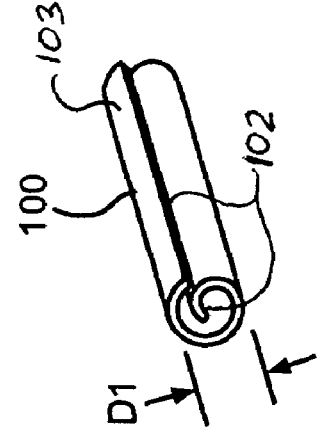
FIG. 2A   FIG. 2B   FIG. 2C

SELF CONTRACTING STENT

RELATED APPLICATIONS

This application claims the benefit of U.S. Provisional Application No. 60/651,028, filed Feb. 8, 2005.

BACKGROUND OF THE INVENTION

The present invention relates to a stent used to ensure a desired inner diameter of a tubular organ or bodily lumen, and in particular, to a method for delivering and recovering the stent.

Stents are often employed to maintain the internal diameter of a bodily lumen, and in particular, to maintain the expanded internal diameter of a bodily lumen that has been expanded by a related medical procedure. For example, in an angioplasty procedure, a narrowed portion of the coronary arteries may be expanded with an angioplasty catheter. It is then typically necessary to take measures to prevent the expanded portion from being narrowed again. In such a case, an expansion retainer, hereinafter referred to as "stent," is generally used for for ensuring a desired inner diameter of a bodily lumen. For ensuring expansion of, for example, a blood vessel by using a stent formed of stainless steel, the stent may be introduced into a predetermined position of the blood vessel through an angioplasty catheter. In the case of a balloon-expandable stent, a balloon disposed at the distal end portion of the catheter may then be expanded so as to expand the stent to a diameter conforming to the desired inner diameter of the blood vessel. Other types of stents are self-expanding and automatically expand to engage the vessel wall upon release from a delivery catheter.

Once expanded, a typical stent cannot be moved unless an external force is applied to the stent. Thus, it may be quite difficult to remove a stent left in the blood vessel, even after recovery of the body part to which the surgical operation was applied. In addition, it can be very difficult to change the position of the stent once it has been deployed and expanded. This may be problematic if the stent has been placed in an erroneous position or location during the initial deployment.

In some instances, stents used in the gastrointestinal system are constructed of plastic, allowing them to be retrieved and/or replaced during a follow-up procedure. However, plastic stents have two disadvantages. First, plastic stents are typically not expandable. In other words, plastic stents cannot be expanded like the self-expanding or balloon-expandable stents described above. Second, the diameter of a plastic stent is limited by the delivery system, typically a catheter, especially if delivered through an endoscope (~11.5 French maximum). Due to the limited diameter of endoscopically delivered plastic stents, these stents are often prone to clogging (e.g., stents deployed in the bile or pancreatic duct) and may have to be replaced every three months, or even more frequently.

In other instances, larger diameter self-expanding stents have been delivered in vivo and deployed in the gastrointestinal system. Because of their larger expanded diameter, such metal stents remain patent longer than plastic stents, averaging perhaps 6 months before clogging. These types of stents are based on a self-expanding metal skeleton typically constructed of a metal alloy such as stainless steel or nitinol. In order for the larger diameter stents to collapse into delivery systems, various mesh or wire geometries are employed. However, the wire and mesh geometries allow for tissue ingrowth, rendering the stent essentially "permanent." When the stent becomes occluded, an additional stent (metal or plastic) can be deployed through the inner lumen of the clogged stent. Accordingly, these types of self-expanding stents are typically only utilized for the palliation of malignancies.

Therefore, a need exists for an expandable stent that can be efficiently and safely removed after some weeks or months in the body, thereby allowing the deployment of the stent in benign situations.

BRIEF SUMMARY

The present invention is defined by the following claims, and nothing in this section should be taken as a limitation on those claims. By way of introduction, the preferred embodiments described below relate to a method for delivering and recovering a stent from a treatment site. The method includes delivering a stent comprising a shape memory material to a treatment site with an expandable device such as a balloon catheter. The method also includes expanding the stent at the treatment site using the balloon catheter so that the stent is attached to the treatment site, and contracting the stent by altering the temperature of the stent to a transition temperature, enabling re-positioning or recovery of the stent from the treatment site. In one aspect of the invention, the stent is contracted by raising the temperature of the stent above a transition temperature. In another aspect of the invention, the stent is contracted by increasing the temperature of the stent above a transition temperature that is above body temperature but below a tissue harming temperature.

The preferred embodiments further relate to a self-contracting stent for use at a treatment site comprising a shape memory material. The stent may have an initial diameter, an expanded diameter, and a contracted diameter at or above a transition temperature of the stent. The contracted diameter is less than the expanded diameter and permits re-positioning or removal of the stent from the treatment site.

BRIEF DESCRIPTION OF SEVERAL VIEWS OF THE DRAWINGS

FIGS. 1A-1C each depict a side view of a self-contracting stent before expansion (1A), after expansion (1B), and after contraction (1C) in accordance with one embodiment.

FIGS. 2A-2C each depict a perspective view of a self-contracting stent before expansion (2A), after expansion (2B), and after contraction (2C) in accordance with one embodiment.

Figure 3A:
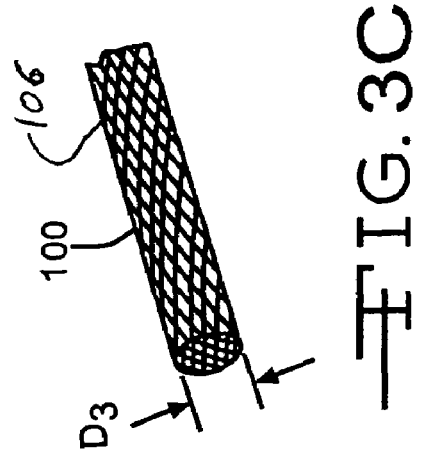
FIGS. 3A-3C each depict a perspective view of a self-contracting stent before expansion (3A), after expansion (3B), and after contraction (3C) in accordance with one embodiment.

It should be appreciated that for simplicity and clarity of illustration, elements shown in the figures have not necessarily been drawn to scale. For example, the dimensions of some of the elements are exaggerated relative to each other for clarity. Further, where considered appropriate, reference numerals have been repeated among the figures to indicate corresponding elements.

DETAILED DESCRIPTION

The present invention disclosed herein involves a self-contracting stent made of a shape memory material, such as nitinol. Shape memory materials are capable of returning to a previously defined shape or size when subjected to an appropriate thermal treatment. For example, a shape memory material having an initial shape or configuration above a first transition temperature may be deformed at a temperature below a second transition temperature of the material to a second configuration. Then, upon heating above the first transition temperature, the material may "remember" and spontaneously return to its initial state. The basis for this behavior is a substantially reversible phase change that occurs when the temperature of the material moves below and above its transition temperatures. U.S. Pat. Nos. 3,174,851, 3,652,969, and 4,304,613 provide additional background information about shape memory materials and are incorporated herein by reference.

Generally, the memory effect is one-way, which means that the spontaneous change from one configuration to another occurs only upon heating. (To obtain a second configuration at a temperature below a transition temperature, it is generally necessary to apply stress.) However, it is possible to obtain a two-way shape memory effect, in which a shape memory material spontaneously changes shape upon cooling as well as upon heating.

According to one embodiment of the invention involving a self-contracting stent, a one-way shape memory effect may be exploited. The initial state may be a contracted configuration of the stent. Also according to this embodiment, a first transition temperature of the stent may be above body temperature, but below a temperature that would harm tissue adjacent to the stent. In the contracted configuration, the stent may be delivered to a treatment site within a bodily vessel. Then the stent may be expanded by applying stress to the stent, e.g., with a rigid dilator or with the balloon of a balloon catheter. In order to retrieve the stent, the temperature of the stent may be brought above the appropriate transition temperature, at which point the stent may return to its initial contracted state or at least to a compressed state sufficient to allow removal of the stent from the body lumen. The temperature of the stent may be changed by injecting a warm fluid to the target site, or by another means, as discussed below. The temperature of the fluid or other means is preferably below tissue harming temperature.

In an alternative embodiment, the two-way shape memory effect may be exploited. According to this embodiment, the initial state may be a contracted configuration of the stent, and a first transition temperature of the stent may be above body temperature but below a temperature that would harm tissue adjacent to the stent. In this configuration, the stent may be delivered to a treatment site within a bodily vessel in its contracted initial state, preferably within a sheath to constrain the stent from expanding spontaneously during delivery. (With the two-way shape memory effect, there may be a change in shape during cooling below a second transition temperature as well as during heating above a first transition temperature. Because the transition temperatures of the stent are above body temperature, according to this embodiment, the stent may be cooled and thus spontaneously change shape upon delivery into the body.) Once the stent is positioned at the site of interest, the sheath may be retracted and the stent may expand spontaneously at body temperature due to the two-way shape memory effect. If desired, an expansion device such as a balloon may be used to aid in the expansion of the stent. In order to retrieve the stent, the temperature of the stent may be brought above the first transition temperature, at which point the stent may return to its initial contracted state or at least to a compressed state sufficient to allow removal of the stent from the bodily lumen. The temperature of the stent may be changed by injecting a warm fluid to the target site, or by another means, as discussed below. The temperature of the fluid or other means is preferably below tissue harming temperature.

In an another embodiment, the two-way shape memory effect may also be exploited. According to this embodiment, the initial state may be an expanded configuration of the stent, and a first transition temperature of the stent may be at or below body temperature. The stent may contract spontaneously upon cooling below a second transition temperature of the stent, due to the two-way shape memory effect. In this contracted configuration, the stent may be delivered to a treatment site within a bodily vessel. The stent may be constrained for delivery to prevent spontaneous expansion of the stent as it is warms up within the bodily vessel. For example, the stent may be delivered to the treatment site within a sheath. Once the stent is positioned at the site of interest, the sheath may be retracted and the stent may expand spontaneously at body temperature to the expanded configuration (its initial state). In order to retrieve the stent, the temperature of the stent may be brought below the second transition temperature, at which point the stent may return to a contracted state, again due to the two-way shape memory effect. Preferably, the amount of contraction is sufficient to allow removal of the stent from the body lumen. The temperature of the stent may be changed by injecting a cooling fluid to the target site, or by another means, as discussed below. The temperature of the fluid or other means is preferably above tissue harming temperature.

The stent may be both self-expanding and self-contracting. The stents described above that exploit the two-way shape memory effect may both self-contract and self-expand. In another example of a stent that may self-expand and self-contract, the stent may be comprised of more than one shape memory material, and each shape memory material may have a different transition temperature to return to an initial state. Each shape memory material may exhibit a one-way shape memory effect. For example, the stent may be comprised in part of a first shape memory material that expands to an initial state at or above a first transition temperature, and in part of a second shape memory material that contracts to an initial state at or above a second transition temperature. The first and second shape memory materials may have different compositions and/or different processing histories.

FIGS. 1A-1C, 2A-2C, 3A-3C, and 4A-4C collectively depict a self-contracting stent 100 for deployment at a treatment site of a tubular organ or body lumen, such as a vessel 150 (see, for example, FIGS. 5-8), before expansion (A), after expansion (B), and after contraction (C), in accordance with various embodiments.

The stent 100 is formed from a shape memory material such as a Ni—Ti alloy (e.g., Nitinol), Cu—Al—Ni alloy, or a Cu—Zn—Al alloy. The shape memory alloy may exhibit a one-way or two-way shape memory effect. Preferably, the stent 100 may consist of a Ni—Ti binary alloy. For example, the alloy may include about 51 atomic % of Ni. The balance may be substantially Ti. Additionally, the the binary alloy may include very small concentrations of elements other than nickel or titanium, such as, e.g., a few parts per million of copper. Alternatively, the stent 100 may be made of a ternary or quaternary Ni—Ti alloy which includes one or more additional alloying elements, such as, for example, Al, Ag, Au, Cu, Fe, Ga, Ir, Nb, Pd, Pt, Rh, Ta, or W. According to one embodiment, the stent 100 may include more than one shape memory alloy.

Preferably, the initial diameter $D_1$ of the stent 100 may be between 0.1 mm and 10 mm, and more preferably between 1 mm and 3 mm. As will be explained in greater detail below, the initial diameter $D_1$ permits the stent 100 to be introduced and positioned within a patient's body lumen 150 (see FIGS. 5-8). The stent 100 may be expanded to, and maintain, an expanded shape having an expanded diameter $D_2$ in the radial direction, as shown, for example, in FIG. 1B. The expanded diameter $D_2$ is greater than the initial diameter $D_1$. Preferably, the expanded diameter may be between 1.5 and 20 mm, and more preferably between 2 and 10 mm. As will be explained in greater detail below, the expanded diameter $D_2$ is typically selected to achieve and maintain the desired expansion of the patient's bodily lumen 150 (see FIGS. 5-8). According to one embodiment, such as when the shape memory material of the stent exhibits a one-way shape memory effect, expansion of the stent 100 may be accomplished mechanically with an expandable delivery device such as balloon catheter. Alternatively, the shape memory material may exhibit a two-way shape memory effect, and the stent may self-expand below a second transition temperature.

When the temperature of the stent 100 is raised above the first transition temperature, the stent 100 may contract to, and maintain, a contracted shape having a contracted diameter $D_3$ as shown, for example, in FIG. 1C. The contracted diameter $D_3$ is less than the expanded diameter $D_2$, and preferably may be between 0.1 mm and 10 mm, and more preferably between 1 mm and 3 mm. Because the contracted diameter $D_3$ is less than the expanded diameter $D_2$, the stent 100 may be removed from the treatment site and repositioned or extracted from the patient with greater ease. In one embodiment, the initial diameter $D_1$ is within about 30% of the contracted diameter $D_3$. Of course, it should be understood that the initial diameter $D_1$ may also be substantially equal to the contracted diameter $D_3$.

Figure 6:
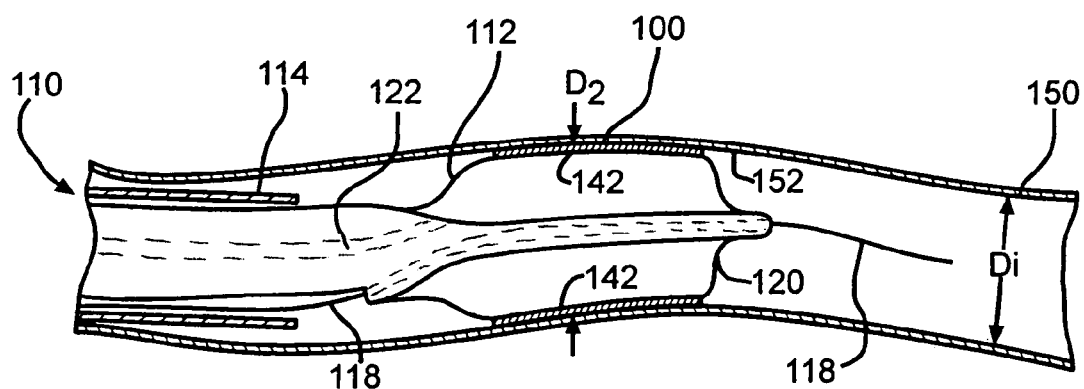
FIG. 6 depicts a partial cross-sectional view of the delivery system depicted in FIG. 5 illustrating a balloon of the delivery system in an inflated position for expanding the stent at the treatment site in accordance with one embodiment.
Figure 7:
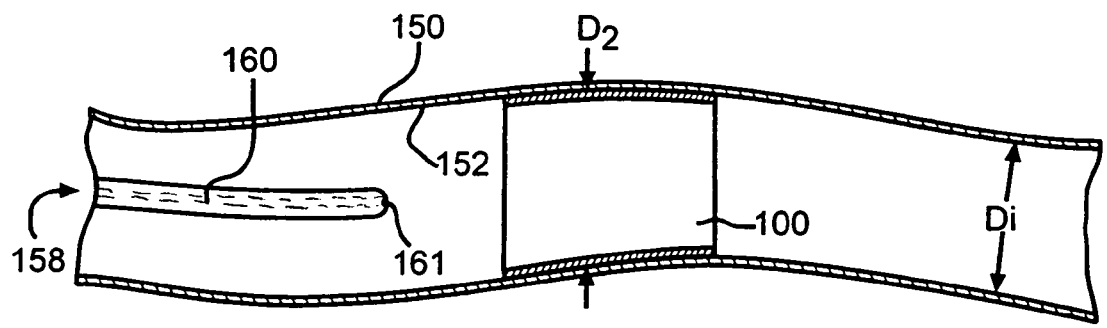
FIG. 7 depicts a partial cross-sectional view of the expanded stent depicted in FIG. 6 and a warming lumen used to raise the temperature of the stent in accordance with one embodiment.
Figure 8:
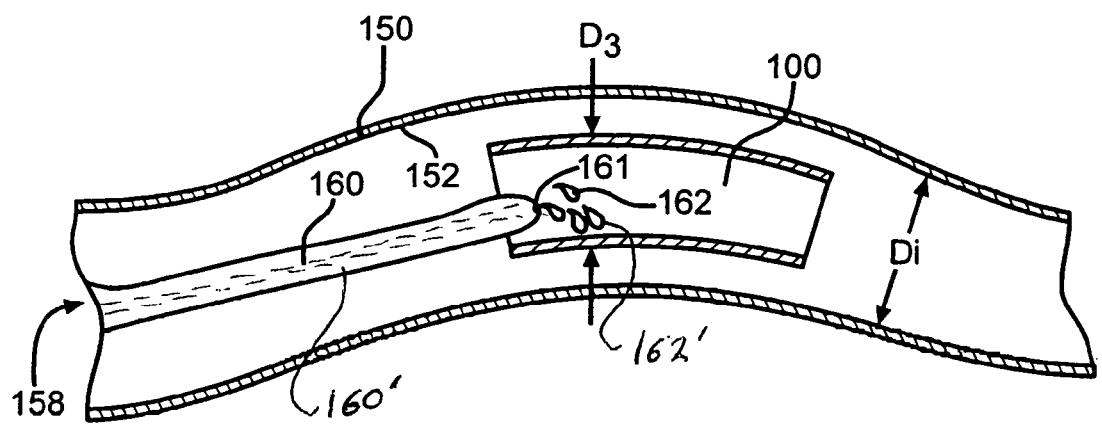
FIG. 8 depicts a partial cross-sectional view of the expanded stent depicted in FIG. 7 in a contracted position after being warmed by fluid from the warming lumen in accordance with one embodiment.

The inner diameter, length, etc. of the stent 100 may be determined to appropriately to conform to the inner size of the bodily lumen or vessel 150 at the treatment site at which the stent 100 is to be attached. In short, the stent 100, when in the expanded state, should have an expanded diameter $D_2$ substantially conforming to the inner diameter $D_1$ of the vessel 150, as illustrated in FIGS. 6 and 7. Additionally, the stent 100, when in the contracted state, should have a contracted diameter $D_3$ small enough to permit the stent 100 to be readily repositioned within or removed from the vessel 150, as illustrated in FIG. 8.

According to one embodiment, the first transition temperature is above body temperature but below a temperature that would harm bodily tissue adjacent to the stent, i.e., above about 35° C. and below about 100° C. More preferably, the first transition temperature is above about 37° C. and below about 75° C., and most preferably above about 40° C. and below about 60° C. Preferably, the second transition temperature is less than the first transition temperature, but above body temperature, according to one embodiment.

In an alternative embodiment, the stent 100 comprises a first transition temperature that is about or below body temperature, but above a tissue harming temperature, i.e., below about 35° C. and above about 0° C. In this embodiment, the initial state or shape of the stent 100 may be an expanded shape having an initial diameter. More specifically, the stent 100 of this particular alternative embodiment may achieve and maintain a contracted shape when below a second transition temperature, such as, for example, when cooled below the normal 35° body temperature, due to the two-way shape memory effect. The stent may return to the initial shape (or to an expanded shape having a diameter typically within about 30% of the initial diameter) in a bodily vessel at a temperature at or above the first transition temperature of the stent.

The stent 100 disclosed herein can use a multitude of geometries and shapes, including solid-wall geometries such as a coiled tube and a cylindrical tube, that are configured to inhibit or prevent tissue in-growth. In one embodiment, the stent 100 may have a spiral-wound or coiled tube shape, as shown in FIGS. 1A-1C.

Referring to FIG. 1A, the stent 100 may be formed by spirally winding a flat wire of a shape memory material into an initial shape having an initial diameter $D_1$ in the radial direction. According to this embodiment, the initial shape is a contracted configuration. The stent 100 of this embodiment may comprise a coiled tube shape that is formed from a flat wire 104 that has been helically wound to form a spring shaped tube. The flat wire 104 has a nominal thickness and width, e.g., between about 0.01 mm and about 0.1 mm in thickness, and between about 0.1 mm and about 3 mm in width. In this particular embodiment, the stent 100 expands from the initial state of diameter $D_1$ to an expanded state of diameter $D_2$, and then contracts from the expanded state to the contracted state of diameter $D_3$, by a change in the diameter of each coil.

The shape of the stent 100 is not restricted to a spiral or coiled tube, however, so long as the stent 100 is substantially cylindrical when in an expanded state. For example, the stent 100 may have a spiral cross section with a diameter $D_1$ when in an initial state, as shown in FIG. 2A, and a cylindrical shape or cross section with a diameter $D_2$ when in an expanded state, as shown in FIG. 2B. The stent 100 may contract to a diameter $D_3$ and have a spiral cross section, as illustrated in FIG. 2C. More specifically, the stent 100 shown in FIGS. 2A-2C comprises a solid sheet of material 103 that has been curved to form a generally C-shaped cross-section with two longitudinally opposing edges 102, wherein the edges 102 overlap with each other in the initial and contracted states (FIGS. 2A and 2C, respectively), and abut with each other in the expanded state (FIG. 2B). However, it should be appreciated that the opposing edges 102 do not have to abut with each other in the expanded state. For example, the opposing edges 102 could be spaced apart from each other, thereby creating a gap therebetween. Likewise, the opposing edges 102 could still overlap with each other, although with a smaller or larger overlap than is shown in FIGS. 2A and 2C. In this particular embodiment, the stent 100 expands from the initial state to the expanded state, and contracts from the expanded state to the contracted state, by a change in the cross-sectional curvature or radius of the sheet material 103. The actual size (i.e., planar dimensions) of the sheet material 103 may not altered, although some expansion or contraction of the material may still occur. One possible advantage of the stent 100 of FIGS.

2A-2C is that the overall length of the device may not change as a result of the expansion or contraction.

Figure 3B:
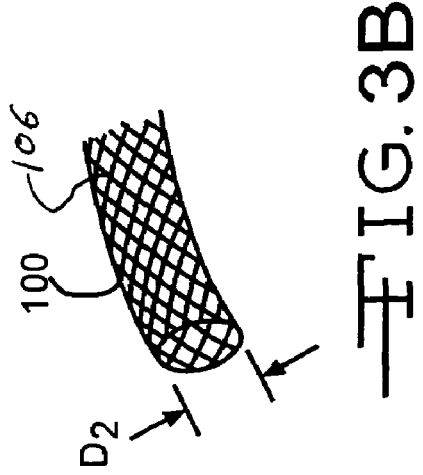
Figure 3C:
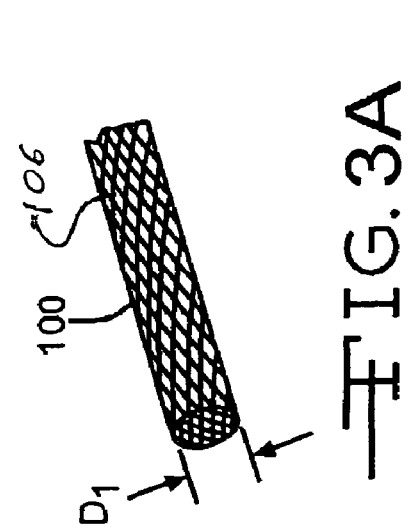

The stent 100 may also be shaped as a net having one or more shape memory alloy wires 106 that are woven or otherwise formed into a cylindrical mesh body, as shown in FIGS. 3A-3C. Such a stent structure, comprising a net, mesh, struts, or similar open structure, may also be formed by laser cutting procedures known in the art. In this case, the stent may be expanded from the initial state having a diameter $D_1$, shown in FIG. 3A, to the expanded state having a diameter $D_2$, shown in FIG. 3B, when the stent 100 is expanded in the radial direction. The stent 100 may then be contracted to a diameter $D_3$, as shown in FIG. 3C, for repositioning within or removal from the vessel.

Figure 4A:
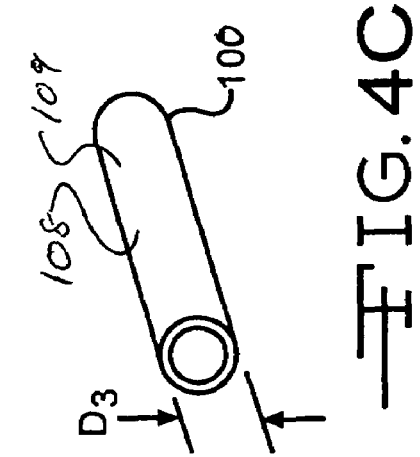
FIGS. 4A-4C each depict a perspective view of a self-contracting stent before expansion (4A), after expansion (4B), and after contraction (4C) in accordance with one embodiment.
Figure 4B:
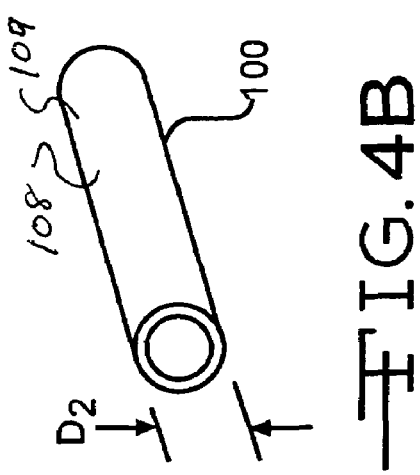
Figure 4C:
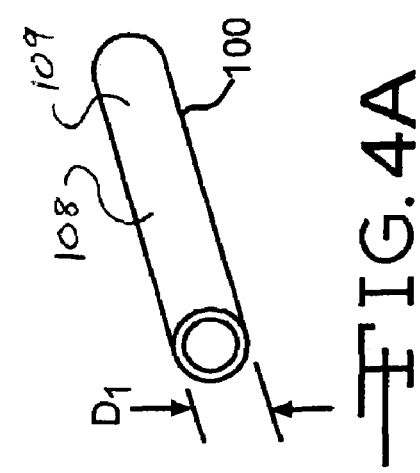

Alternatively, the stent 100 may comprise a tube or pipe-like shape formed from a substantially solid sheet of material 108. Like the other embodiments described above, the pipe may have an initial state having a diameter $D_1$, as shown in FIG. 4A, and may be expanded to an expanded state having a diameter $D_2$, as shown in FIG. 4B. Following expansion, the pipe may later be contracted to a contracted state having a diameter $D_3$, as shown in FIG. 4C. The stent 100 may have a polymer covering or coating 109 disposed over the outer surface of the stent to ease the delivery to and positioning of the stent 100 at the treatment site.

The stent 100 may be processed and annealed in a constrained state to obtain a pre-set configuration or initial state that the material may "remember." During manufacture, the stent 100 may be drawn and deformed a controlled amount and heat treated or annealed. A typical annealing treatment involves holding the stent 100 at a temperature lower than the melting temperature of the stent 100, such as, for example, 400° C. to 700° C., for a number of hours. hours. The stent 100 may require several rounds of drawing and annealing to optimize the properties of the stent and to acquire a final form to be "remembered," also referred to as the initial state or the initial shape. The annealing may not change the transition temperatures, which may be predetermined by the raw material used to make the stent 100.

A delivery system 110 is used to deliver the stent 100 to a treatment site within a tubular organ or lumen of a living body, such as vessel 150. The delivery system 110 may be capable of mechanically expanding the stent 100 from an initial state to an expanded state. The delivery system may include devices capable of mechanically expanding the stent 100, such as a rigid dilator and a balloon catheter. A balloon catheter 112 and balloon 120 are shown, for example, in FIGS. 5 and 6. In some embodiments, the delivery system may include a sheath disposed about the stent 100. Upon retraction of the sheath at the treatment site, the stent 100 may self-expand to an expanded configuration. The delivery system may also include a temperature changing device 158, as illustrated, for example, in FIG. 7. The temperature changing device 158 may be any device which can be used to change the temperature of the stent 100, such as a heating apparatus, a cooling apparatus, an electrical device, or a lumen which carries either hot or cold fluid.

Figure 5:
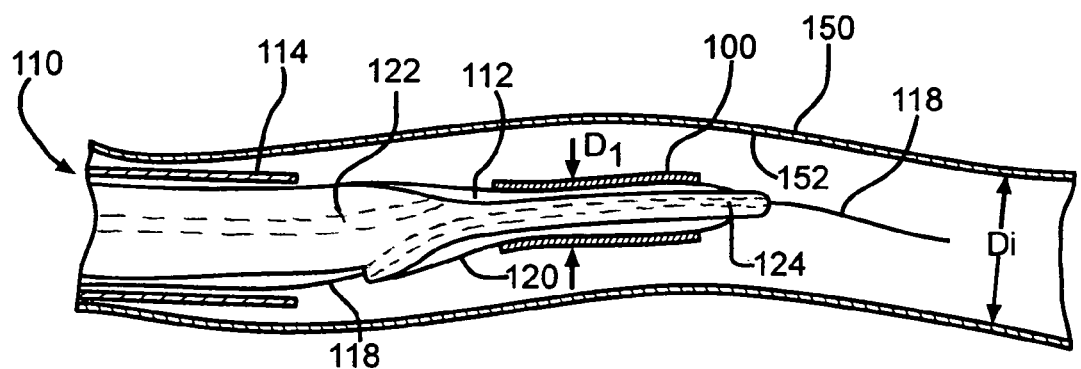
FIG. 5 depicts a partial cross-sectional view of a delivery system for delivering a self-contracting stent to a treatment site in a vessel in accordance with one embodiment.

In one embodiment, the delivery system 110 comprises a guide catheter 114 and a balloon catheter 112. The delivery system 110 is designed to deliver the stent 100 to a treatment site, such as vessel 150, with the aid of the guide catheter 114 and the balloon catheter 112, as illustrated in FIGS. 5 and 6. The treatment site is any site upon which a stent may be delivered to, and includes vessels and body cavities, and in particular the ducts of the gastrointestinal system and the coronary arteries. Preferably, the guide catheter 114 has a diameter of between 0.1 and 10 mm and a length of between about 100 to 1500 mm. Preferably, the guide catheter tube 14 is formed of, for example, ethylene-vinyl acetate copolymer. The delivery system 110 may deliver the stent 100 to and from any of a number of vessels or bodily lumens, such as, for example, through the patient's esophagus and into the common bile duct, or from a patient's right groin and through the length of an artery to the aorta and coronary arteries.

Through the guide catheter 114, a wire guide 118 may be first advanced into the corresponding vessel 150. Preferably, the wire guide 118 is between 100 mm and 1500 mm in length. The wire guide 118 serves as instrumentation track to guide the balloon catheter 112. The wire guide 118 may have a central lumen, not shown, for pressure measurement or to contain a contrast medium.

The balloon catheter 112 includes a balloon 120 attached at one end to an inflation lumen 122 and attached at an opposing end to a wire guide lumen 124. The wire guide lumen 124 forms a passage sealed off from an interior of the balloon 120. The passage enables the balloon 120 to be coupled to and pushed along the wire guide 118, and thereby be guided along the wire guide 118 to the target site. To minimize frictional resistance between the interior of the passage of the wire guide lumen 124 and the surface of the wire guide 118, the inside of the passage of the wire guide lumen 124 and/or exterior surface of the wire guide 118 may be provided with a lubricant coating. Preferably, the balloon 120 is between 5 and 100 mm in length, and the inflation lumen 122 is between 100 and 1500 mm in length. The balloon 120 tapers from both ends to an active region 142 around which the stent 100 is mounted, as illustrated in FIGS. 5 and 6. The active region 142 of the balloon 120 is the region which contacts and presses against the inside of the stent 100, and expands the stent 100 against an inner wall 152 of the vessel 150, when the balloon 120 is expanded, as illustrated in FIG. 6.

The inflation lumen 122 has an opening, not shown, into the interior of the balloon 120. The inflation lumen 122 serves firstly to transmit thrusts and tensions for pushing the balloon 120 to and fro along the wire guide 118, and for rotating the balloon 120 within the vessel 150. For this reason, it may be desirable for the inflation lumen 122 to be reinforced by a stabilizing wire, not shown. Besides the function of transmitting forces, the inflation lumen 122 is used to inject fluids into the interior the balloon 120 in order to inflate the balloon 120, and used for the aspiration of fluids from the balloon 120 when the diameter of the balloon 120 is to be decreased. Preferably, the inflation lumen 122 is sealingly connected with the balloon 120 so as to prevent fluids from leaking out of the balloon 120.

The balloon catheter 112 also includes a wire guide lumen 124 adapted to receive the wire guide 118 in a sliding fit arrangement. The wire guide lumen 124 traverses the interior of the balloon 120 from one end of the balloon 120 to the other end of the balloon 120, as illustrated in FIGS. 5 and 6. Preferably, the wire guide lumen 124 is sealingly separated from the interior of the balloon 120, so as to prevent fluids within the interior of the balloon 120 from leaking out through the wire guide lumen 124. Preferably, the inflation lumen 122 is integrally connected with the wire guide lumen 124 at one end of the balloon 120, as illustrated in FIGS. 5 and 6. The wire guide 118 enters the guidewire lumen 124 at one end and exits the guidewire lumen 124 at the opposing end, as illustrated in FIGS. 5 and 6. In alternative embodiments of the balloon catheter 112, the wire guide lumen 124 may extend proximally from the balloon 120 along the length of and adjacent to the inflation lumen 122. In still other embodiments of the balloon catheter 112, the wire guide lumen 124 may be completely disposed distally of the balloon 120, or may be eliminated altogether. It should also be understood that other types of expandable devices other than balloons can be utilized.

When delivering a stent 100 to a treatment site, such as a constriction or stenosis in a vessel or bodily lumen, the balloon 120 and balloon catheter 112 are introduced into the vessel 150 in much the same way as described above. However, for this task, the stent 100 is mounted around the active region 142 of the balloon 120, as illustrated in FIG. 5. When mounted on the balloon catheter 112, the stent 100 is in the initial state having a diameter $D_1$, Once the balloon 120 is delivered to the treatment site, the balloon 120 is inflated, causing the stent 100 to expand at the treatment site so that the stent 100 is pressed against the inner wall 152 of the vessel 150, as illustrated in FIG. 6. When so deployed, the stent 100 is in the expanded state having a diameter $D_2$. The diameter $D_2$ of the stent 100 in the expanded state generally equals the inner diameter $D_1$ of the vessel 150. It should, however, be appreciated that the diameter $D_1$ of the vessel 150 may be altered by deployment and expansion of the stent 100. Upon expanding the stent 100, the balloon 120 is then deflated and retracted into the guide catheter 114, leaving the stent 100 at the treatment site, as shown in FIG. 7.

In order to remove or reposition the stent, a temperature changing device 158 may be introduced into the vessel 150, as illustrated in FIG. 7. The temperature changing device 158 may be any device which can be used to change the temperature of the stent 100, such as a heating apparatus, a cooling apparatus, an electrical device, or a lumen which carries either hot or cold fluid. Upon changing the temperature of the stent 100 to above or below a first transition temperature of the stent 100, the stent 100 may contract, as illustrated in FIG. 8. More specifically, the stent 100 is in a contracted state having a diameter $D_3$. Once contracted, the stent 100 can be removed from the vessel 150 with a forceps or other grasping device (not shown). Since the diameter $D_3$ of the stent 100 in a contracted state is less than the inner diameter $D_1$ of the vessel 150, the stent 100 may be readily removed from the vessel 150 or re-positioned within the vessel 150 without causing damage to the vessel 150. Preferably, the stent 100 is removed or re-positioned using a retractable grabber or forceps which are secured to the stent 100. Upon securing the grabber or forceps to the stent 100, the stent may be re-positioned or removed by retracting it into a catheter with an overtube that fits through an endoscope. Advancing the overtube over the stent 100 helps minimize trauma when removing the stent 100. Preferably, the stent is secured to the grabber or forceps before changing the temperature of the stent 100 above the first transition temperature of the stent 100.

In one embodiment, the temperature changing device 158 is a warming lumen 160 (see FIGS. 7-8). The warming lumen 160 carries a hot fluid 162 that may be used to raise the temperature of the stent 100 to at least a first transition temperature. The first transition temperature may be, for example, above body temperature but below a tissue harming temperature. Upon introducing the warming lumen 160 into the vessel 150, the warming lumen 160 may dispense the hot fluid 162 onto the stent 100, and the temperature of the stent 100 may be increased above the first transition temperature. Upon reaching a temperature at or above the first transition temperature, the stent 100 may contract, as illustrated in FIG. 8. Upon contraction, the stent 100 may be removed from the vessel 150.

In an alternative embodiment, the temperature changing device 158 may be a cooling lumen 160' (see FIG. 8). The cooling lumen 160' carries a cold fluid 162' used to lower the temperature of the stent 100 below a second transition temperature. The second transition temperature may be, for example, below body temperature but above a tissue harming temperature. Upon introducing the cooling lumen 160' into the vessel 150, the cooling lumen 160' may dispense the cold fluid 162' onto the stent 100, and the temperature of the stent 100 may be lowered. Upon reaching a temperature at or below the transition temperature, the stent 100 may contract, as illustrated in FIG. 8. Upon contraction, the stent 100 may be removed from or repositioned within the vessel 150. According to this embodiment, the stent may have self-expanded within the vessel and a balloon catheter 112 (or another expansion device) may not have been used.

Although the invention has been described and illustrated with reference to specific illustrative embodiments thereof, it is not intended that the invention be limited to those illustrative embodiments. Those skilled in the art will recognize that variations and modifications can be made without departing from the spirit of the invention.

The invention claimed is:

1. A method for delivering and recovering a stent within a bodily vessel, the method comprising the steps of:
    a) providing a stent of an initial diameter, the stent comprising a two-way nickel-titanium shape memory alloy having a first transition temperature and a second transition temperature, the second transition temperature being below the first transition temperature;
    b) delivering the stent to a treatment site within a patient;
    c) expanding the stent at the treatment site to an expanded diameter larger than the initial diameter by cooling to or maintaining at a temperature below the second transition temperature; and
    d) heating the stent to at least the first transition temperature, thereby contracting the stent to a contracted diameter smaller than the expanded diameter.

2. The method of claim 1, further comprising the steps of:
    e) repositioning the stent within the treatment site; and
    f) re-expanding the stent to a second expanded diameter, the second expanded diameter being larger than the contracted diameter.

3. The method of claim 1, further comprising the step of:
    e) removing the stent from the treatment site.

4. The method of claim 1, wherein the first transition temperature is above body temperature but below a tissue harming temperature.

5. The method of claim 1 wherein the step of expanding the stent includes using an expandable device.

6. The method of claim 5, wherein the expandable device is a balloon catheter.

7. The method of claim 1, wherein the step of delivering the stent to a treatment site comprises disposing a sheath about the stent to constrain the stent from expanding, the stent expanding when cooled to or maintained at a temperature below the second transition temperature.

8. The method of claim 7, wherein the step of expanding the stent comprises retracting the sheath, the stent being at the temperature below the second transition temperature.

9. The method of claim 1, wherein the heating step is carried out by using a warming device.

10. The method claim 9, wherein the warming device comprises a catheter having a lumen for the delivery of a warm solution to the treatment site.

11. The method of claim 1, wherein the contracted diameter and the Initial diameter are not the same.

* * * * *

UNITED STATES PATENT AND TRADEMARK OFFICE
CERTIFICATE OF CORRECTION

PATENT NO.         : 7,524,329 B2
APPLICATION NO.    : 11/348278
DATED              : April 28, 2009
INVENTOR(S)        : Brian K. Rucker It is certified that error appears in the above-identified patent and that said Letters Patent is hereby corrected as shown below:

In the Claims

In column 10, claim 1, line 26, before "the second transition" insert --both temperatures being above body temperature,--.

In column 10, claim 5, line 46, immediately after "method of claim 1" insert --,--.

In column 10, claim 11, line 64, before "diameter are not the same" delete "Initial" and substitute --initial-- in its place.

Signed and Sealed this

Twenty-fifth Day of August, 2009

David J. Kappos
*Director of the United States Patent and Trademark Office*